United States Patent [19]

Goldberg et al.

[11] Patent Number: 4,457,624

[45] Date of Patent: Jul. 3, 1984

[54] SUSPENDED SEDIMENT SENSOR

[75] Inventors: Marvin C. Goldberg, Englewood; Kirk M. Cunningham, Lakewood, both of Colo.

[73] Assignee: The United States of America as represented by the Secretary of the Interior, Washington, D.C.

[21] Appl. No.: 376,851

[22] Filed: May 10, 1982

[51] Int. Cl.$^3$ ............................................. G01N 15/02
[52] U.S. Cl. .................................... 356/336; 356/342
[58] Field of Search ............... 356/335, 336, 338, 339, 356/341, 342, 343, 427; 73/57, 432 PS

[56] References Cited

U.S. PATENT DOCUMENTS

| | | | |
|---|---|---|---|
| 2,379,158 | 6/1945 | Kalischer | 356/335 X |
| 3,518,437 | 6/1970 | Riggs | 356/343 X |
| 3,869,209 | 3/1975 | Sighist | 250/574 X |

OTHER PUBLICATIONS

Granatstein et al., "Multiple Scattering of Laser Light from a Turbid Medium," *Applied Optics*, vol. 11, No. 5, pp. 1217–1224, 5/72.

Lewis et al., "A Microcomputer-Modified Particle Size Spectrometer", *J. Aerosol Sci.*, vol. 9, No. 5, pp. 391–397, 10/78.

*Primary Examiner*—Davis L. Willis
*Assistant Examiner*—Matthew W. Koren
*Attorney, Agent, or Firm*—Thomas Zack

[57] ABSTRACT

A suspended sediment sensor system for determining concentrations of particles and their size distribution in a submitted fluid sample. The particles being measured range from 50–1000 microns in dimensions and the concentrations range from <50 to 50,000 parts per million (ppm) of fluid. Equipment used includes a fall tube, laser light source, light scattering detector system, optical equipment, and a system to control the movement of the sample and other fluid past the laser and detector system. The detector system measures background scatter from particles impinged upon by the laser source at an angle of about 165°. Contemplated to be used with the foregoing is a computer and associated controls to allow an unattended in situ system for a river, lake, etc.

4 Claims, 3 Drawing Figures

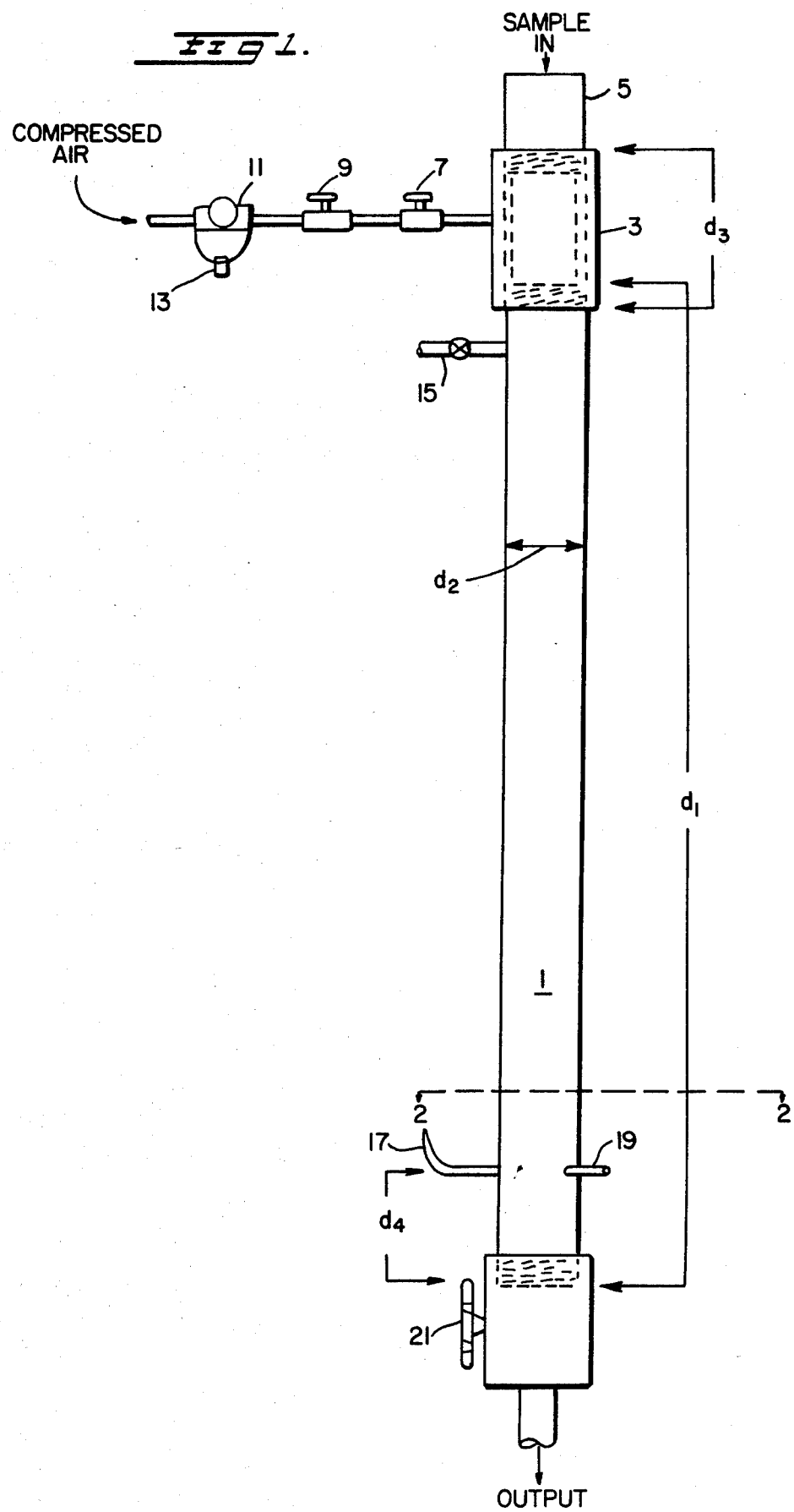

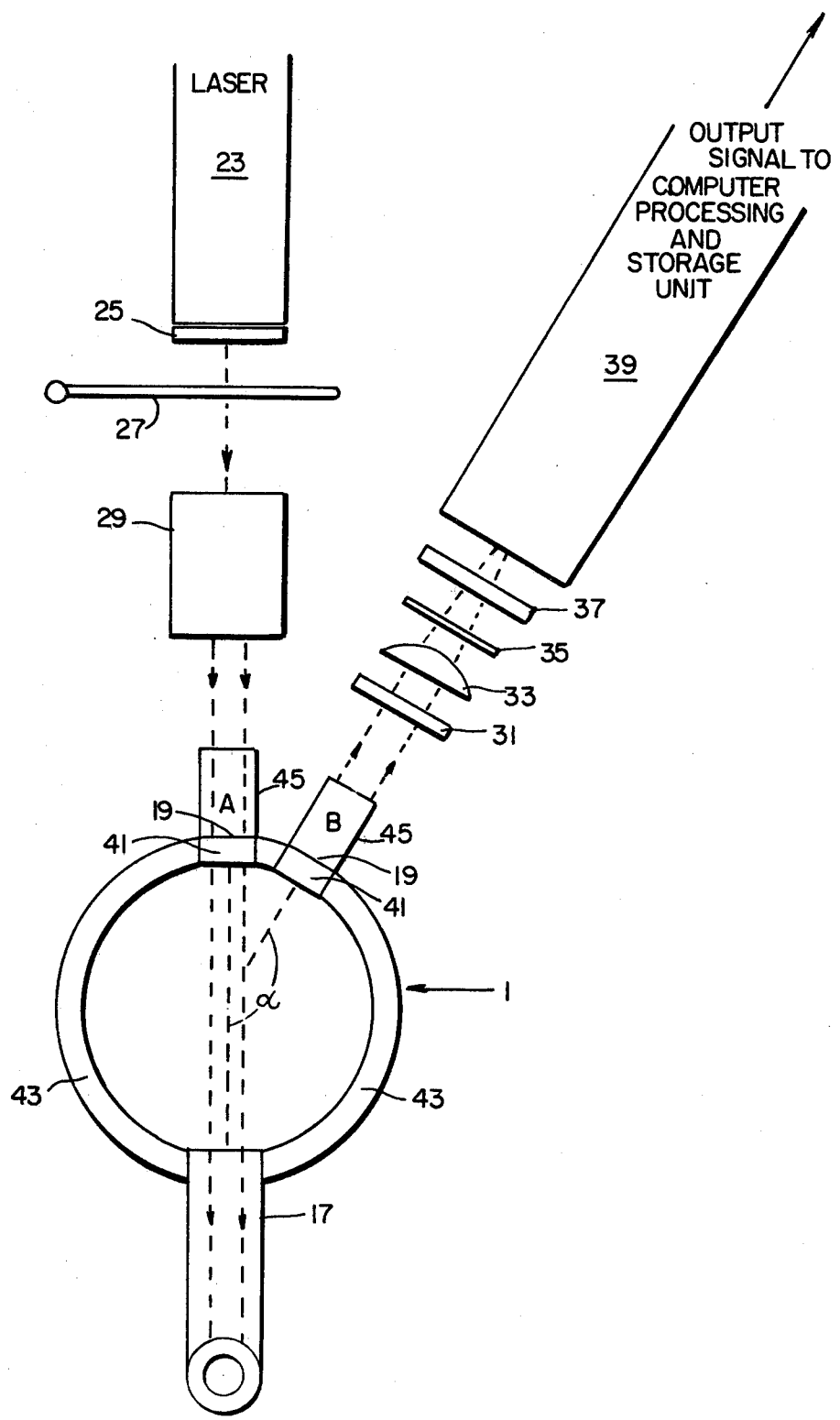

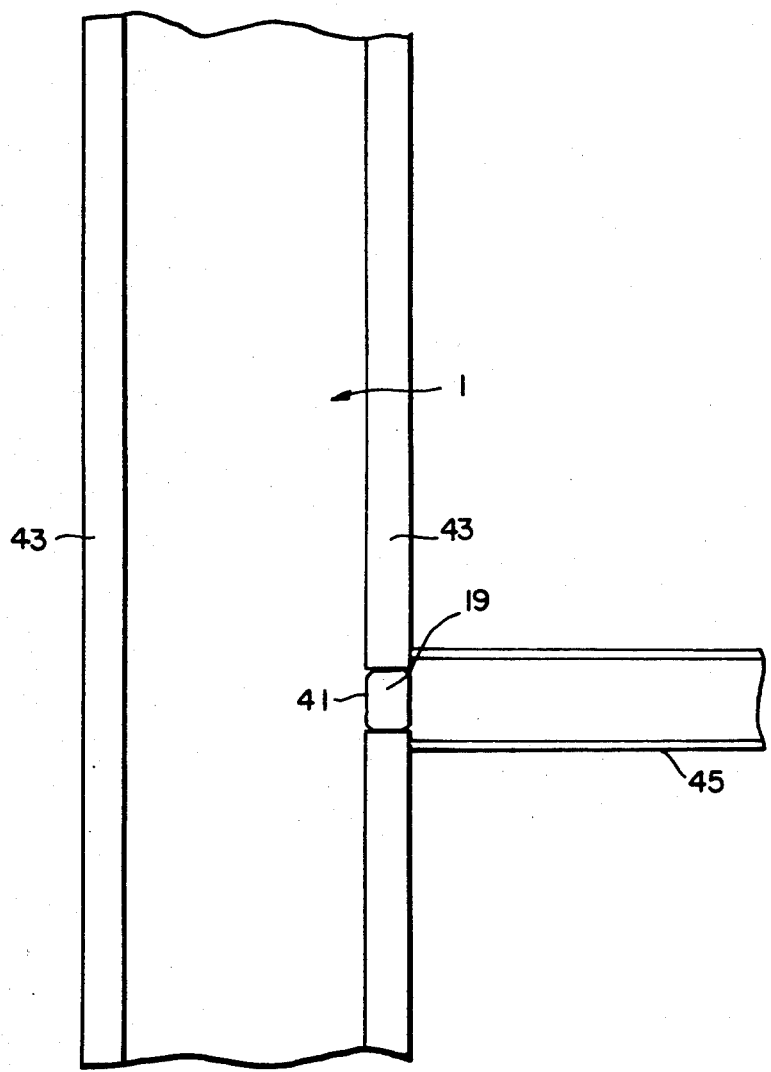

SUSPENDED SEDIMENT SENSOR

BACKGROUND OF THE INVENTION

The invention disclosed herein is a sensor employing the principle of laser backscattering and sedimentation to determine particle size/mass distribution of particulate matter suspended in liquids.

DESCRIPTION OF THE PRIOR ART

Many known devices utilize the principles of light scattering or sedimentation alone or light scattering or sedimentation in conjunction with other physicl methods to define particle size/mass distributions. Chapters 9, 10, 12 and 14 of the book entitled "Particle Size Measurement," by Terence Allen, Chapman and Hall, 1974, discusses many of these combinations and permutations in detail. One reference of which we know employs the same general technique as that which we employ herein, i.e., light scattering in combination with sedimentation. This reference is entitled "The Use of Scattered Light in the Determination of the Distribution of Sizes of Particles in Emulsions," by Alfred J. Stamm et al and is found in the Journal of the American Chemical Society magazine, Volume 47, pages 1582–96 (1925). They illuminated a square glass cell from opposite sides with two Mazda lamps that are a polychromatic light source. The sample was uniformly suspended by vigorous shaking and the scattered light measured at 90° from the incident light by photographic plates. This device differs from our device in several important respects. Their particle size sensing range was 0–8 microns, ours is 50 to 100 microns. Our invention uses a laser light source rather than a Mazda lamp which gives our invention several advantages. The laser is more power stable and does not require frequent calibration; it can concentrate high power density on a small area to allow almost point interrogation of the sample. The Stamm et al device detects the scattered light by photographic readout of a homogeneous mixture as it settles out, whereas our invention detects the fall at a fixed point through a distilled water column allowing a much higher sensitivity to detection of large particles because our scattered signal is detected over a very low background and their device tries to detect a small decrease in signal from a very large initial signal. Our system can measure large particles with good accuracy, the other device cannot. Further, our invention uses photoelectric detection which is much more sensitive and give a continuous readout. The Stamm et al reference discloses the use of photographic detection which is noncontinuous and provides an integrated reading over the time period of the photographic exposure. By use of photoelectric detection, our invention can be made to operate continuously and unattended much more readily than the Stamm et al system.

Some devices, referred to as photosedimentometers, measure sedimentation and turbidimetry for particle sizing. With such equipment, turbidimetry is used to measure the portion of the light beam passing through the sample which is not scattered. This results in a sensitivity disadvantage when compared against scattering since turbidimetry measures a small variation in a large signal whereas scattering represents a substantial increase of light signal on top of a negligible background. Our use of the back angle of detection, i.e., 165° or greater, is a significant improvement, because as a solution becomes more dense, it becomes more opaque to light. As the angle of detection becomes less than 165° then it becomes necessary to correct for the change in scattering light path as a function of increasing sample concentration. It further becomes necessary to correct for forward diffraction scattering. At back angles, the backscattered radiation retains the high scattered light intensity in high solution concentrations even though the light path is reduced and forward diffraction scattering is not a significant factor.

This invention can be adapted to continuously monitor particle concentrations in hydrologic systems in situ over a wide range of sizes, shapes, and concentrations. More specifically, it allows a particle measurement range from 50–1000 microns; and a concentration range from <50 to 5,000 parts per million (ppm) and upwards to greater than 50,000 (ppm) with appropriate sample dilution.

SUMMARY OF THE INVENTION

This is a sensor assembly which employs the principles of light scattering and sedimentation to continuously monitor particle size distributions in fluids. The assembly includes a sample compartment attached to a fall tube with ports therein to admit laser light and detect the scattered light at back angles greater than 165°. A light trap (a light horn) to eliminate the effects of reflection of the incident beam and/or any forward scattered light, is mounted directly in line with the incident beam but on the opposite side of the fall tube. A laser assembly with filters and a beam expander is used as the light source. Backscattered radiation caused by particles as they pass through the beam of the laser light in the fall tube is measured by a photomultiplier tube and appropriate signal handling devices. Using various calibration curves, it is possible to calculate a histogram of particle mass versus fall diameter. It is also possible to automate the system to make up to 20 measurements per 24-hour period in situ and unattended.

DESCRIPTION OF THE DRAWINGS

FIG. 1 is a schematic diagram of part of the system viewed from the side.

FIG. 2 is a view taken along lines 2—2 of FIG. 1 looking downwardly showing the sensor/detector assembly used therewith.

FIG. 3 is an enlarged partial cross-sectional view of one of the light ports.

DESCRIPTION OF THE PREFERRED EMBODIMENT

The purposes of our invention are: to monitor particle concentrations and particle sizes in hydrologic systems such as rivers, lakes, regulated waterways, oceans, and the like; to obtain a sediment size profile that includes the mass concentration per size range as well as the overall mass concentration; to monitor over a wide range of sizes, shapes, and particulate concentrations found in natural water systems; and to do so in situ on a batch basis whose turnaround time is short enough to approximate continuous measurement.

The basic scheme and principles relating to this invention are as follows: initially a long vertically oriented fall tube is filled with water at the same temperature and solute composition as that of the sample. Next, a water sample containing the sediment under consideration is placed in the top chamber of the fall tube. At time zero, the sediment falls down through the tube at a rate described by Stroke's Law (i.e., where the resisting force R is given by the relation $R = 6\pi\eta rv$ where $\eta$ is the viscosity of fluid, r the radius of the particle, and v the relative velocity of the particle and fluid). After passing down through most of the fall tube, the particles encounter a horizontally directed, vertically polarized laser beam which enters the fall tube through an optical window. This light impinges on the sample particles in a specific orientation. At a "back" angle $\alpha$ greater than 165°, another optical window is placed in the tube wall in the same horizontal plane as the incident laser light window. The lser light which has been scattered by the sediment is passed through this second window and focused onto the surface of a photomultiplier tube. The orientation of the detector with respect to the laser beam (i.e., the angle $\alpha$) is critical to the operation of our invention. This electronically detected scattered radiation is next analyzed by computers and mathematical formulas to arrive at the resultant particle size and particle concentration, for each resolvable size range. This results in a mass assignment to each size range and thus characterizes the sample. As indicated heretofore, two objectives are sought by our invention. The first is to measure the total sediment concentration per known volume of sample water. The second is to determine the sediment concentration for each particle size (in small size increments) per known volume of sample water, and thus be able to determine the sediment size distribution per weight of sediment sample. The applicable measurement ranges we are concerned with are from 50 to 1000 microns for the particle's mean diameter; and a concentration range from <50 to 50,000 ppm of water. With proper design, a system employing our invention can be fully automated to perform in an unattended manner in situ for periods of weeks giving as many as 20 measurements of different samples per 24-hour period.

The apparatus to practice the perferred embodiment of our invention is shown in FIG. 1 and FIG. 2. In an actual working embodiment, both figures would be operatively joined together in a working system. However, for ease in understanding, the FIG. 1 system does not show the laser light source, the light detectors, and associated electronics. In FIG. 1 there is shown the galvanized steel fall tube 1 which has been painted inside with black epoxy-based marine paint. Near the upper end of the fall tube is a 2-inch "Mini-Flex" valve 3 which can be closed by 40 pounds of air pressure. It is made from a steel body with a rubber sleeve. Above this valve is a section of pipe 5 into which the sample slurry is deposited for measurement. A three way manual ball valve 7 is connected by appropriate tubing to valve 3. Its function is to release and introduce compressed air from and into the space around the rubber sleeve of valve 3. In fluid communication with this manual valve is a two-way manual ball valve 9 for controlling the flow of compressed air to valve 7. Further upstream is the air pressure gage 11 for the incoming compressed air and below it is the oil trap 13. Jointed to the vertical fall tube is the overflow tube 15, the light trap 17, the two ports 19 (only one is shown which is the entrance port A) to admit the laser light to the fall tube and an exit port to detect its scattered portions, and the hand operated rubber disc brass valve 21 for emptying the fall tube. The ports are situated such that they are in the same general horizontal plane, spaced near to each other in the fall tube wall and with an angle of observation or a back angle greater than 165° (angle $\alpha$ in FIG. 2). In one working embodiment, the dimensions indicated as $d_1$, $d_2$, etc. had the measurements $d_1 = 3$ feet, $d_2 = 2$ inches, $d_3 = 7$ inches, and $d_4 = 5$ inches.

FIG. 2 depicts the fall tube with an added light source, detectors, electronics, and associated devices as they would appear, if installed, when viewed along line 2—2 of FIG. 1 when looking downward along the vertical axis of the fall tube 1. The same light trap 17 for the light beam and the two ports 19 of FIG. 1 are also shown so that the interrelation between the cooperating parts will be clearer. The helium-neon laser 23 has a long-wave pass filter to absorb blue plasma radiation from the laser. This is not essential, but allows illumination with a more monochromatic light source. Next, there is a shutter 27 and beam expander 29 which provides for the output with a beam diameter of about $\frac{1}{4}$ inch towards the fall tube. The left most port A, aligned with the beam expander and fall tube, serves as the entrance for the light beam. The right most port B serves as an observation port for back-scattered laser light. Both ports are $\frac{1}{8}$ NPT brass nipples enclosing 0.305 inch glass windows. The glass windows in Port A has an anti-reflection coating on its outside.

In addition to port B, the FIG. 2 detector system employs a shutter 31, a lens 33, a polarizing sheet 35, a series of neutral density filters 37, and a red-sensitive photomultiplier 39. Lens 33 serves to collimate scattered light from the fall tube volume and polarizing sheet 35 polarizes this collimated light in a direction parallel to the light beam polarization. The series of neutral density filters 37 have the following percentiles of light transmission to the photomultiplier tube 100 (no filters), 49.3, 23.8, 10.1, and 4.4. These filters adjust the light intensity to match the detection range of the analog to digital converter in a signal analysis system.

FIG. 3 is an enlarged partial cross-sectional view of either one of the light ports A or B. Since the ports per se are identical, the same description applies to both. A lens 41 within an opening in the fall tube wall 43 allows transmitted or scattered light, as the case may be, to be transmitted through the wall. A light shield 45 extends out from the tube at the location of the port and functions to prevent interference from ambient light sources.

The operation of the FIG. 1 system with the FIG. 2 apparatus incorporated therein—i.e., the perferred embodiment of our invention—will now be explained for particles in the disclosed range and greater than 50 microns. The intensity of the parallel detected scattered light is a function of fall time. Using various calibration curves, this measured intensity data will permit the calculation of a histogram of particle mass concentration versus fall diameter. Initially, with valves 3 and 21 open, the fall tube is flushed out with about 1 liter of distilled (or nonparticle containing) water. Distilled water can be used or water of the same ionic strength of solution, pH, temperature, and solute composition as the sample water keeping in mind that this "distilled" or other water must be particle-free. Valve 21 is closed and about 2 liters of distilled water are placed in the fall tube to fill it up to the overflow tube 15. Valve 3 is then closed. Using the FIG. 2 laser and detector system, the background scatter for this pure water is measured near the bottom of the fall tube. These measured light intensity readings are taken over a time frame of several seconds, and the results may be stored in a computer. Thereafter, 200 milliters (ml) of sample slurry is poured into the pipe section 5 above valve 3. Next, at what can be considered zero time, valve 3 is rapidly opened by using the compressed air valve 7 and computer data taking is started. Both the fall tube, tf, and intensity, I°(tf), measurements continue until the smallest particle of interest has passed by the laser/detector system of FIG. 2. For 50 micron particles this may be as long as 6 minutes. Typically, the measurements would be made at 0.1 second intervals for the first minute or so and then for 1 or 2 second intervals thereafter. When the measurement cycle for a given sample is completed, valve 21 is opened and the fall tube is drained and flushed. It is now readly for another charge of water and slurry. The distilled water is used as a system flush to eliminate any possibility of contamination from one sample to another and is measured to allow a data record of the background for the next sample. Essentially this measured raw data allows the following calculation to take place:

$$I(tf) = I°(tf) - B(tf)) \times F \qquad [1]$$

where F is a filter factor to correct for neutral density filter transmission (=1.00 at 100 percent transmission), I°(tf) is the raw intensity measured for a given fall time and sample slurry, and B(tf) is the background intensity for the distilled water sample.

The values of I(tf) for a given sample slurry consisting of a sieved range of particle of mean size $d_m$ (microns) are integrated as a function of time. The fall time at the half-height point ($t_{50}$) on the resulting integrated intensity vs. fall time curve is take as the measure of the fall time for $d_m$. The set of all $t_{50}, d_m$ pairs for sieved samples of various $d_m$ from 50 to 1000 microns are least squares fit by an equation of the form:

$$t_{50} = A + \frac{B}{d_m^{\frac{1}{2}}} + \frac{C}{d_m} + \frac{D}{d_m^{3/2}} + \frac{E}{d_m^2} \qquad [2]$$

This equation allows one to calculate the fall time for any size $d_m$ within the size concentration range of the calibration data. It is valid only for the calibrating material.

The total integrated intensity of each fall curve for each size $d_m$ is divided by the weight of solid in the slurry (a concentration measure works equally well to give the parameter $S_T/g$, integrated intensity per gram. The set of measured $S_T/g$, $d_m$ values is least squares fit by an equation of the form:

$$S_T/g = \frac{A}{d_m^{1.5}} + \frac{B}{d_m^{2.5}} \qquad [3]$$

This equation is valid only for the type of particle used in the calibration and for suspension mass concentrations lower than about 5000 ppm. To measure suspensions of total concentration greater than 5000 ppm, appropriate dilution with particle-free sample water is necessary. We use particle-free sample water as it has the same solute composition, the concentration and pH as the sample water containing the particles but this water does not contain any particles capable of scattering light.

With these two equations for $S_T/g$ and $t_{50}$, one can calculate a mass/size histogram for any suspension as long as the suspension's properties does not exceed the range of validity of the calibrations. The steps in this process are:

(1) Calculate the integrated intensity vs. time from I(tf) vs. t.

(2) Choose particle size ranges of interest and calculate their characteristic fall times from equation (2) (the $t_{50}$ equation).

(3) Find the difference in integrated intensity, $S_T$, between these fall times and calculate a $d_m$ value for the fall time interval.

(4) Calculate g in equation (3) by substituting the values of $d_m$ and $S_T$ found in step 2 and 3 above.

Thus, it has been shown that the system of FIGS. 1 and 2 will allow us to achieve our stated objectives. The exact equipment used can vary. In one working embodiment, the following equipment with the previously given "d" dimensions was used: Laser 23—helium-neon, 2 mw output with beam polarization perpendicular to the plane of FIG. 2; polarizing sheet 35 with a direction of polarization parallel to the light beam polarization; and photomultiplier 39—red-sensitive type RCA No. 8645 operated at the plateau voltage. Other variations and features for the described perferred embodiment are also possible. None should be used to change the scope and spirit of our invention which is to be limited only by the claims that follow.

We claim:

1. A suspended sediment sensor system for measuring particle size distribution in a fluid sample in the range of 50 to 1000 microns and particles concentration from 50 to 50,000 parts per million comprising:

a generally vertical hollow interior fall tube adapted to receive within its hollow portion the fluid sample whose particle size distribution and concentration content is to be measured;

said fall tube having port means near its lower end for admitting laser light thereinto and for detecting the scattered admitted laser light after it impinges upon the particulate matter in the sample;

a source of laser light operatively associated with said port means, said source admitting a collimated generally vertical polarized light beam into the interior of the fall tube in a direction generally perpendicular to the direction particles would fall in the tube;

means mounted in the fall tube for trapping light transmitted across its interior; and a light intensity detector system operatively associated with said fall tube's port means for measuring the intensity of back scattered light from the particles in the sample after being impinged by the laser light beam and outputting electrical signals related thereto, said detector system having a light polarizer operative in the same direction as the impinging polarized lser light and said system being mounted on the fall tube adjacent to the laser source and oriented with respect to the admitted laser beam such that it forms an obtuse angle therewith.

2. The sensor system of claim 1 also including means for controlling the introduction of the sample into the upper portion of the fall tube and separate means in the lower portion of the fall tube for controlling the discharge of the liquid sample after it has passed by the detector system.

3. The sensor system of claim 1 wherein the obtuse angle formed between the admitted laser beams and observed background scattered light in the detector system is at least 165° but less than 180°.

4. The sensor system of claim 1 wherein said port means comprises two adjacent openings in the walls of the fall tube in approximately the same horizontal plane, each of said openings having a lens therein which allows light to pass therethrough with a light shield mounted thereon extending outwardly from the tube.

* * * * *